US010660710B2

(12) United States Patent
Jain et al.

(10) Patent No.: US 10,660,710 B2
(45) Date of Patent: May 26, 2020

(54) ACOUSTIC 3D TRACKING OF INTERVENTIONAL TOOL

(71) Applicant: KONINKLIJKE PHILIPS N.V., Eindhoven (NL)

(72) Inventors: Ameet Kumar Jain, New York City, NY (US); Francois Guy Gerard Marie Vignon, Croton-On-Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1099 days.

(21) Appl. No.: 15/023,943

(22) PCT Filed: Sep. 16, 2014

(86) PCT No.: PCT/IB2014/064537
§ 371 (c)(1),
(2) Date: Mar. 22, 2016

(87) PCT Pub. No.: WO2015/044831
PCT Pub. Date: Apr. 2, 2015

(65) Prior Publication Data
US 2016/0242856 A1    Aug. 25, 2016

Related U.S. Application Data

(60) Provisional application No. 61/881,500, filed on Sep. 24, 2013.

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/4494* (2013.01); *A61B 8/461* (2013.01);
(Continued)

(58) Field of Classification Search
CPC .................. A61B 8/0841; A61B 34/20; A61B 2034/2063
See application file for complete search history.

(56) References Cited

U.S. PATENT DOCUMENTS 4,407,294 A  * 10/1983  Vilkomerson ..... A61B 1/00142
                                                600/461
5,400,788 A     3/1995  Dias
(Continued)

FOREIGN PATENT DOCUMENTS

| EP | 0397960 A1 | 11/1990 |
|----|------------|---------|
| WO | 2012172458 A1 | 12/2012 |
| WO | 2013066821 A2 | 5/2013 |

OTHER PUBLICATIONS

Cheung, Stephanie et al "Enhancement of Needle Visibility in Ultrasound-Guided Percutaneous Procedures", Ultrasound in Medicine & Biology, vol. 30, Issue 5, 2004.

*Primary Examiner* — Jeffrey G Hoekstra
*Assistant Examiner* — Jason M Ip

(57) ABSTRACT

A system and method for tracking an interventional tool based on a spatial alignment of two or more acoustic sensors relative to the interventional tool include operating an acoustic imaging device to generate an acoustic image plane, and operating each acoustic sensor to output a composite acoustic sensing waveform derived from an acoustic sensing of the acoustic beam array. Each composite acoustic sensing waveform can include a plurality of acoustic beam sensing waveforms. The system and method can further include operating a tracking workstation to track a position of the interventional tool relative to the acoustic image plane derived from a waveform profile analysis of the composite acoustic sensing waveforms.

13 Claims, 7 Drawing Sheets

(51) Int. Cl.
*A61B 8/08* (2006.01)
*A61B 90/00* (2016.01)

(52) U.S. Cl.
CPC .......... *A61B 8/5207* (2013.01); *A61B 8/4488* (2013.01); *A61B 8/58* (2013.01); *A61B 2034/2063* (2016.02); *A61B 2090/3929* (2016.02)

(56) References Cited

U.S. PATENT DOCUMENTS

| | | | |
|---|---|---|---|
| 6,546,276 B1 * | 4/2003 | Zanelli | A61B 8/4254 600/407 |
| 2008/0291784 A1 * | 11/2008 | Yamanaka | B06B 1/02 367/99 |
| 2016/0081760 A1 | 3/2016 | Verard | |

* cited by examiner

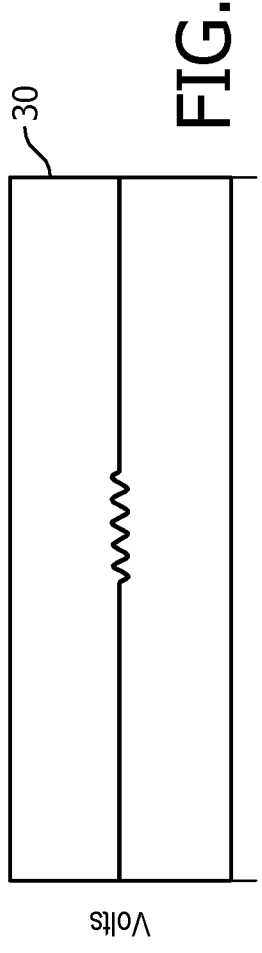
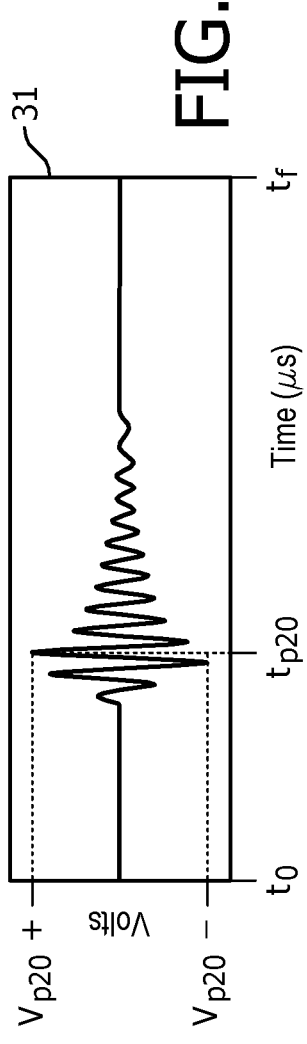
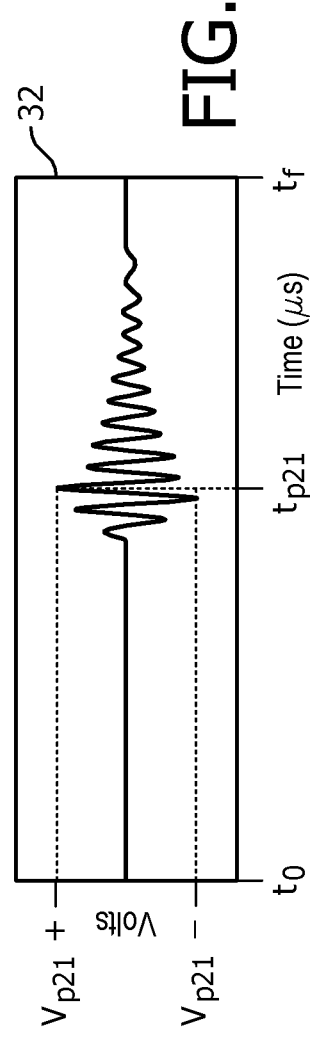
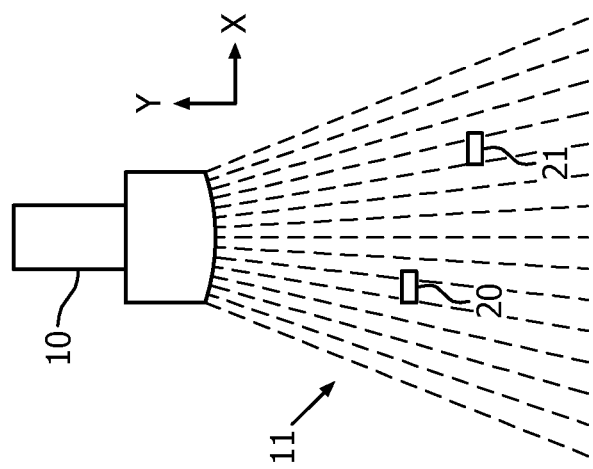
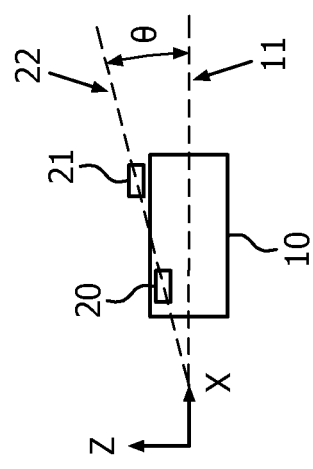

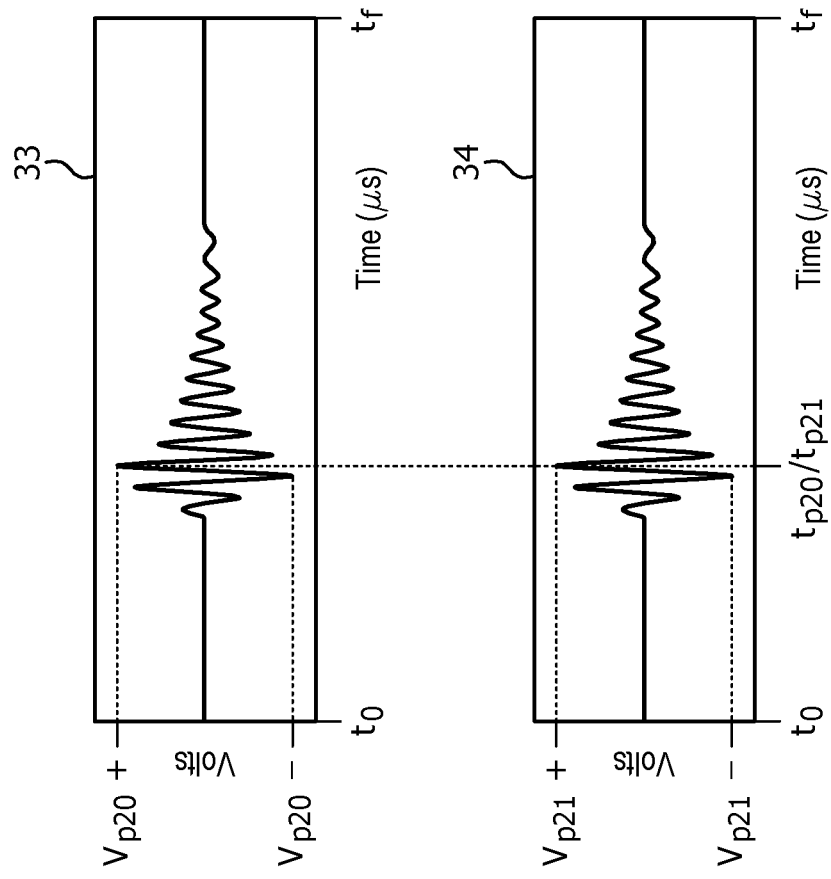
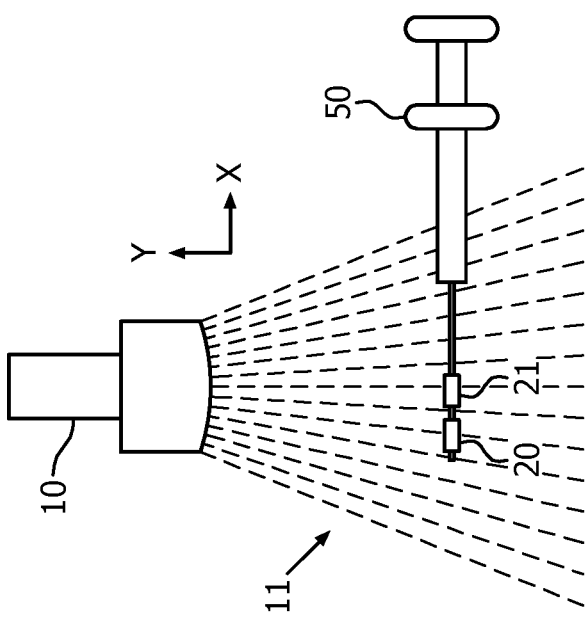
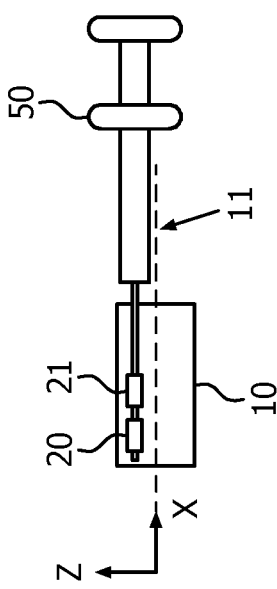
FIG. 5A
FIG. 4A
FIG. 4B

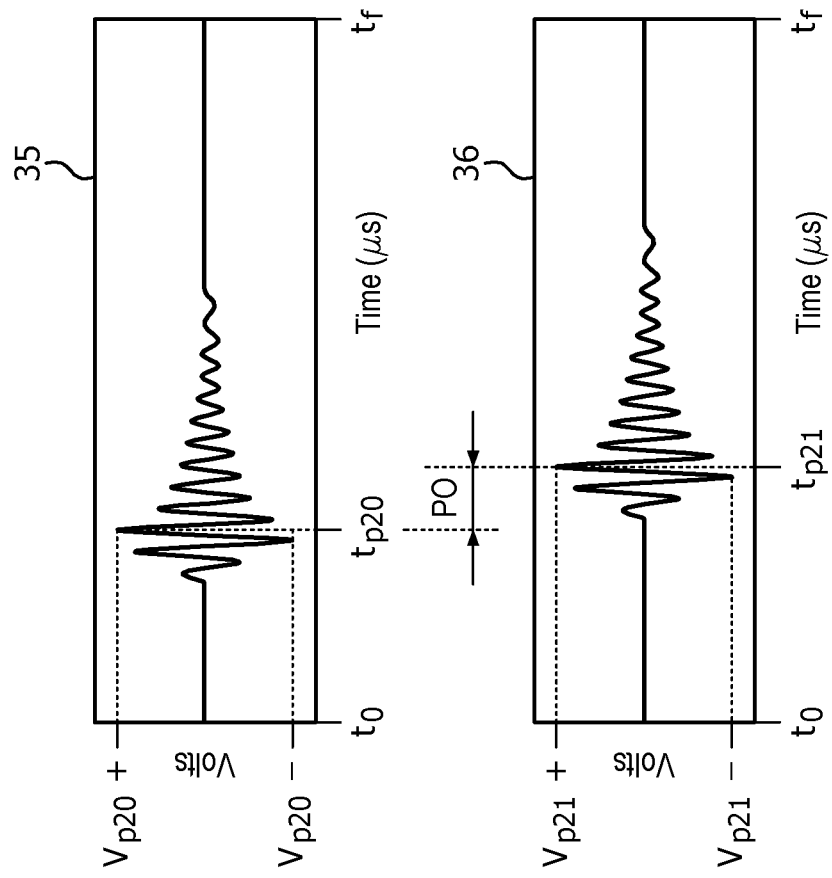
FIG. 5B
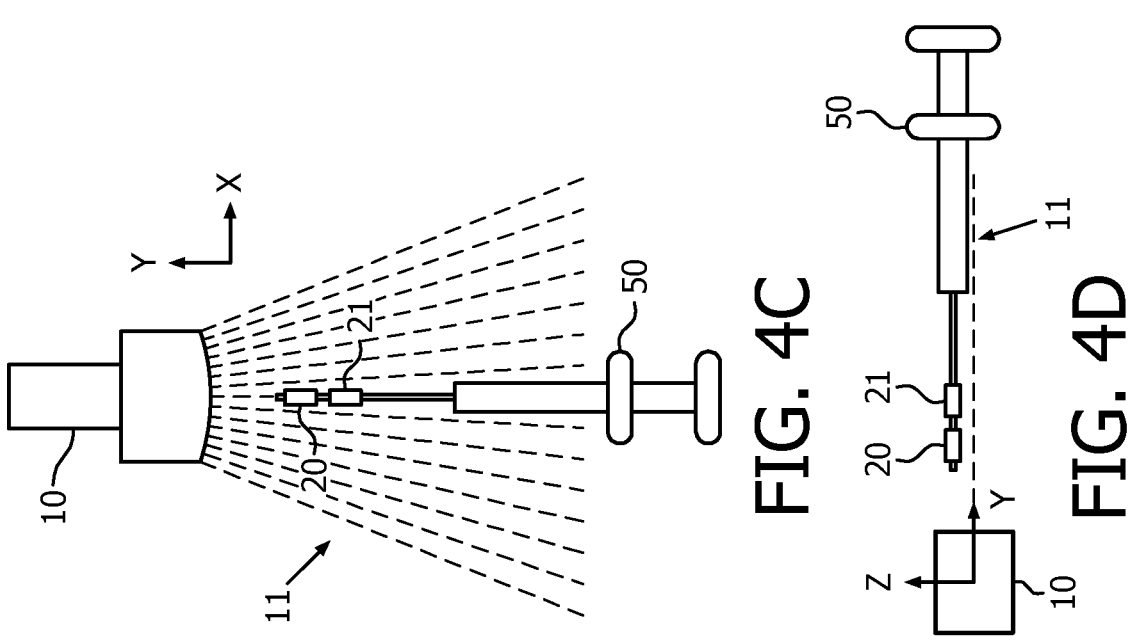
FIG. 4C
FIG. 4D

ACOUSTIC 3D TRACKING OF INTERVENTIONAL TOOL

CROSS-REFERENCE TO PRIOR APPLICATIONS

This application is the U.S. National Phase application under 35 U.S.C. § 371 of International Application No. PCT/IB2014/064537, filed on Sep. 16, 2014, which claims the benefit of U.S. Provisional Patent Application No. 61/881,500, filed on Sep. 24, 2013. These applications are hereby incorporated by reference herein.

The present invention generally relates to a three-dimensional ("3D") tracking of a relative position of an interventional tool (e.g., a needle, a catheter, etc.) to an acoustic image plane generated by an acoustic imaging device (e.g., a two-dimensional ("2D") ultrasound probe having a one-dimensional ("1D") transducer array). The present invention specifically relates to acoustic sensors spatially aligned relative to the interventional tool (e.g., attached to or embedded in a distal tip of a needle or a catheter) to output composite acoustic sensing waveforms derived from an acoustic sensing of the acoustic image plane for purposes of facilitating the relative position tracking of the interventional tool to the acoustic image plane.

A 2D ultrasound probe having a 1D transducer array is commonly used for visualization of a target anatomical plane in a wide range of clinical interventions. However, it is a challenge to assess a position of an interventional tool (e.g., a needle, a catheter, etc.) outside of an acoustic imaging of the target anatomical plane generated by the 2D ultrasound probe. Consequently, a clinician may spend a lot of effort and time in trying to exactly position the interventional tool inside the acoustic image of the target anatomical plane, particularly a distal tip of the interventional tool. More particularly, for interventions involving oblique/orthogonal injection of the interventional tool into the target anatomical plane, it has proven difficult to establish an exact time and position of an entry inside the acoustic image of the target anatomical plane For example, needle insertion under ultrasound guidance is commonly performed for various interventions (e.g., biopsies, fluid drainage, nerve blocks, vascular access, etc.). While needle visualization techniques based on steering imaging beams approximately perpendicular to the needle shaft have been implemented, in a significant number of cases the needle deviates from the acoustic image plane due to tissue heterogeneities and/or bevel asymmetry. Essentially, an out-of-plane needle disappears from the acoustic image plane irrespective of the sophistication of the smart needle visualization enhancement software. The clinician then has to move the acoustical image plane to reacquire an image of the needle, but as a result loses the acoustic image of the target anatomical plane. Furthermore, the clinician does not know where the needle is in relation to the acoustic image plane and therefore the clinician has no indication how to move the 2D ultrasound probe to find the needle.

In summary, for acoustic imaging, it is an imperative operating principle to keep imaging the target anatomical plane and at the same time know the relative position of the needle with respect to the target anatomical plane. The present invention adheres to this operating principle by providing acoustic sensors spatially aligned relative to the interventional tool (e.g., attached to or embedded in a distal tip of a needle or a catheter) to output composite acoustic sensing waveforms derived from an acoustic sensing of the acoustic image plane for purposes of facilitating the relative position tracking of the interventional tool to the acoustic image plane.

According to an exemplary embodiment of the present invention, two or more acoustic sensors are provided spatially aligned relative to an interventional tool (e.g., attached to or embedded in a distal tip of a needle or a catheter). In operation, each acoustic sensor is structurally configured to output a composite acoustic sensing waveform derived from an acoustic sensing of an acoustic image plane (e.g., generated by a 2D ultrasound probe having a 1D transducer array, linear or curved). Each composite acoustic sensing waveform includes an array of acoustic beam sensing waveforms. A tracking workstation can be provided structurally configured to track a position of the interventional tool relative to the acoustic image plane derived from a waveform profile analysis of the composite acoustic sensing waveforms.

Also in accordance with an exemplary embodiment of the present invention, provided is system including an interventional tool (e.g., a needle or a catheter), and two or more acoustic sensors spatially aligned relative to the interventional tool (e.g., attached to or embedded in a distal tip of a needle or a catheter). A tracking workstation can be provided structurally configured to track a position of the interventional tool relative to the acoustic image plane derived from a waveform profile analysis of the composite acoustic sensing waveforms.

In accordance with yet another exemplary embodiment of the present invention, provided is a method for tracking an interventional tool based on a spatial alignment of two or more acoustic sensors relative to the interventional tool (e.g., acoustic sensors attached to or embedded in a distal tip of a needle or catheter). The method involves operating an acoustic imaging device (e.g., a 2D ultrasound probe having a 1D array, linear or curved) to generate an acoustic image plane and operating each acoustic sensor to output an composite acoustic sensing waveform derived from an acoustic sensing of the acoustic beam array. Each composite acoustic sensing waveform includes an array of acoustic beam sensing waveforms. The method further involves operating a tracking workstation to track a position of the interventional tool relative to the acoustic image plane derived from a waveform profile analysis of the composite acoustic sensing waveforms.

The foregoing exemplary embodiments and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

FIGS. 1A and 1B respectively illustrate exemplary top and side views of acoustic sensors sensing an acoustic image plane in accordance with the present invention.

FIGS. 2A-2C illustrate exemplary acoustic beam sensing waveforms outputted by the acoustic sensors shown in FIGS. 1A and 1B in accordance with the present invention.

FIGS. 4A and 4B respectively illustrate a first set of exemplary top and side views of acoustic sensors spatially aligned on an interventional needle sensing an acoustic image plane in accordance with the present invention.

FIG. 5A illustrates exemplary acoustic beam sensing waveforms outputted by the acoustic sensors shown in FIGS. 4A and 4B in accordance with the present invention.

FIGS. 4C and 4D respectively illustrate a second set of exemplary top and side views of acoustic sensors spatially aligned on an interventional needle sensing an acoustic image plane in accordance with the present invention.

FIG. 5B illustrates exemplary acoustic beam sensing waveforms outputted by the acoustic sensors shown in FIGS. 4C and 4D in accordance with the present invention.

Figure 4E:
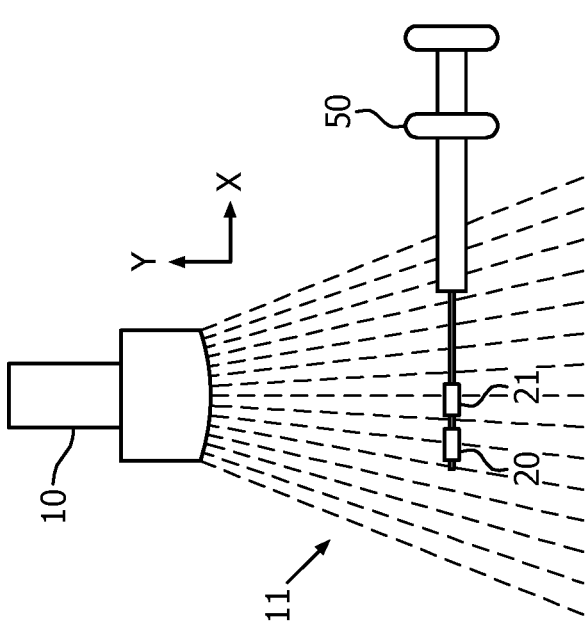
Figure 4F:
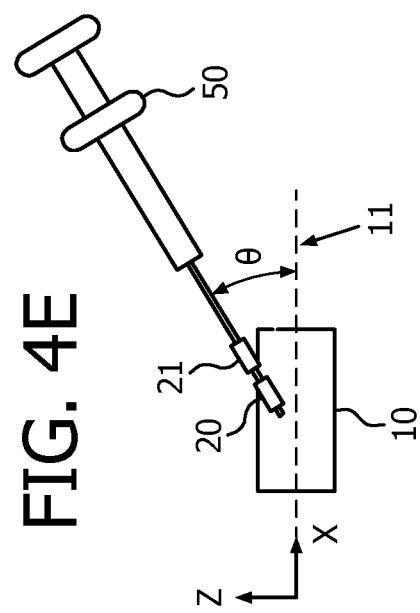

FIGS. 4E and 4F respectively illustrate a third set of exemplary top and side views of acoustic sensors spatially aligned on an interventional needle sensing an acoustic image plane in accordance with the present invention.

Figure 5C:
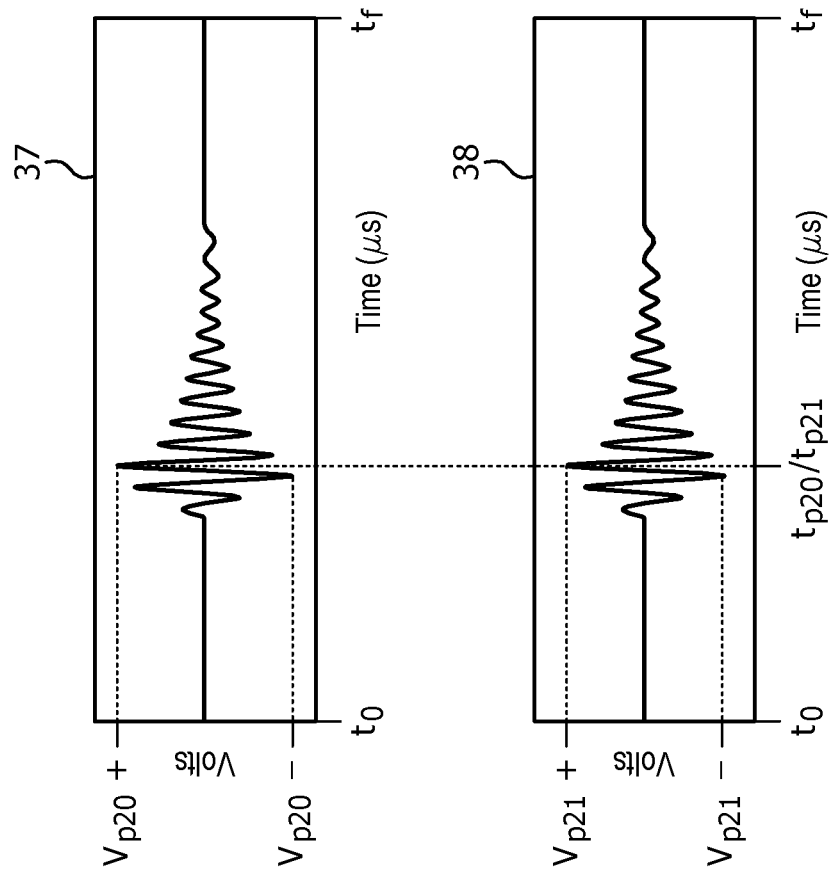

FIG. 5C illustrates exemplary acoustic beam sensing waveforms outputted by the acoustic sensors shown in FIGS. 4E and 4F in accordance with the present invention.

Figure 6:
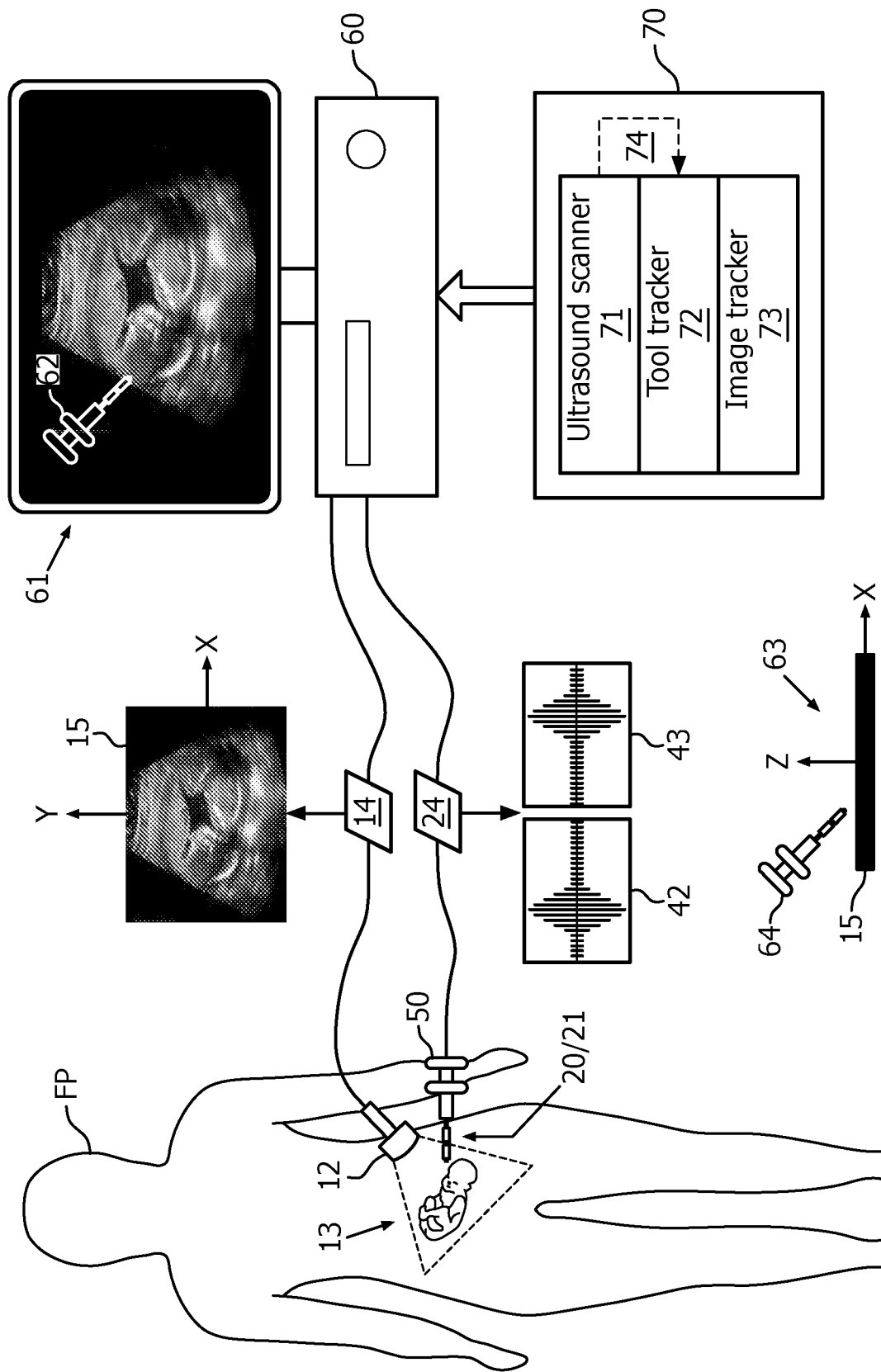

FIG. 6 illustrates an exemplary embodiment of a tracking system of the present invention implementing an interventional procedure.

Figure 7:
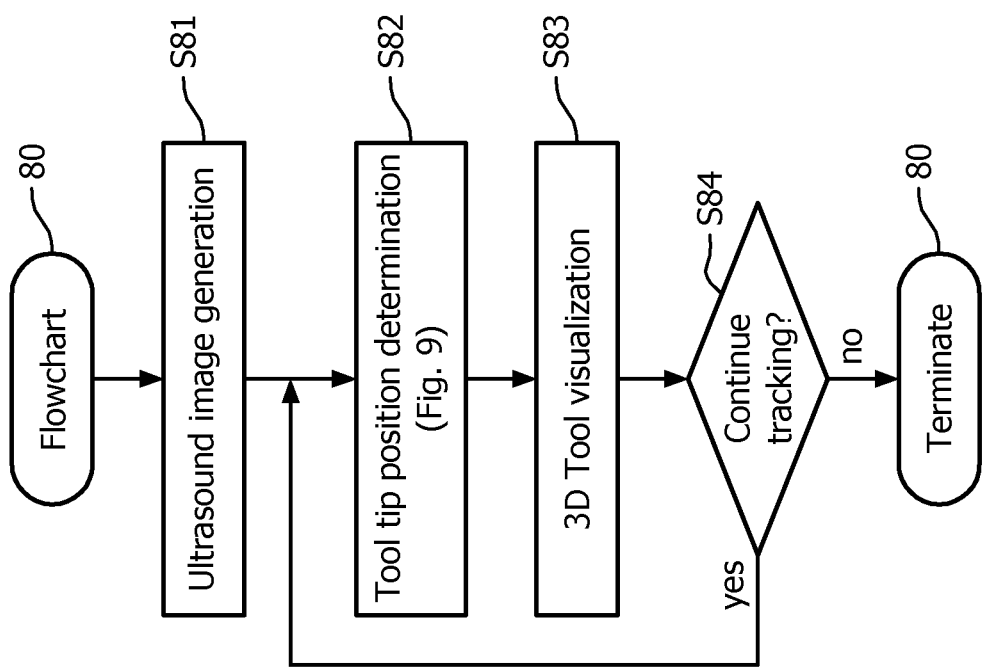

FIG. 7 illustrates a flowchart representative of an exemplary embodiment of an interventional imaging method in accordance with the present invention.

Figure 8:
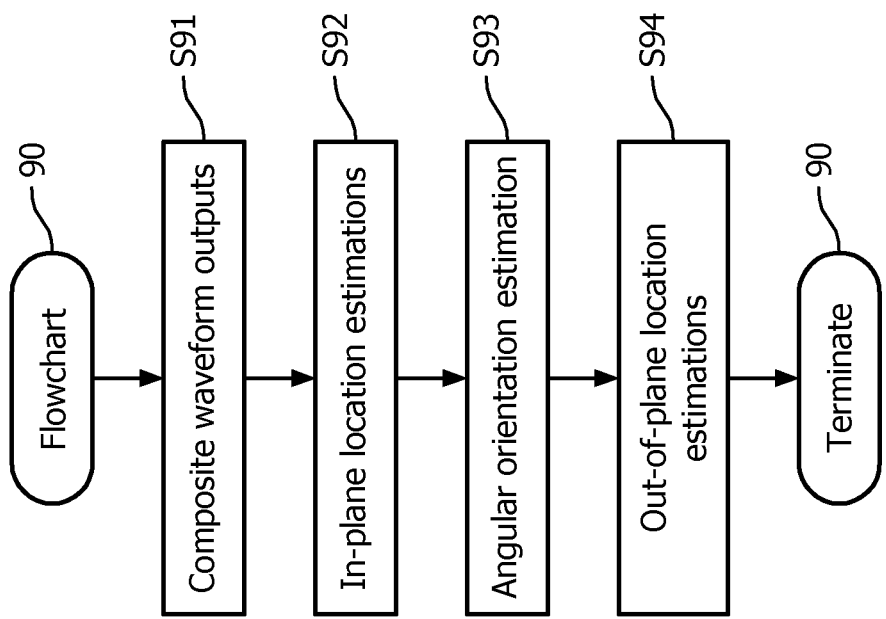

FIG. 8 illustrates a flowchart representative of an exemplary embodiment of an interventional tool tracking method in accordance with the present invention.

Generally, the present invention provides an operable integration of (1) an interventional tool having two or more acoustic sensors attached thereto or embedded therein, (2) an acoustic imaging device for generating an acoustic image plane, (3) a 3D position tracking via the acoustic sensors of the interventional tool relative to the acoustic image plane, and (4) a display of a 3D rendering of the interventional tool superimposed on a 2D acoustic image.

For purposes of the present invention, the term "interventional tool" is broadly defined herein as any tool, device, equipment, etc. utilized for executing any interventional procedure as known in the art. Examples of an interventional tool include, but are not limited to, a needle and a catheter, and examples of interventional procedures include, but are not limited to, biopsies, fluid drainage, nerve blocks, vascular access, etc.

For purposes of the present invention, the term "acoustic sensor" is broadly defined as any device structurally configured to output a waveform representative of a sensing of acoustic energy.

For purposes of the present invention, the term "acoustic imaging device" is broadly defined herein as any device structurally configured for transmitting acoustic energy to visualize subcutaneous body structures (e.g., tendons, muscles, joints, vessels and internal organ, etc.). Examples of an acoustic imaging device include, but are not limited to, a 2D ultrasound probe having a 1D transducer array, linear or curved.

Specifically, the present invention is premised on each acoustic sensor sensing various vibrational strength levels of acoustic energy from acoustic beams generated by the acoustic imaging device as the interventional tool is navigated in proximity to the acoustic image plane. Vibrations of the acoustic sensors caused by the acoustic energy stimulate each acoustic sensor to output an acoustic beam sensing waveform for each acoustic beam whereby each acoustic beam waveform has a profile dependent upon a proximity of the acoustic sensor to a particular vibrational strength level of a corresponding acoustic beam. More particularly, the vibrational strength level of an acoustic beam attenuates as the acoustic beam propagates through an anatomical region.

As the interventional tool is navigated in proximity to the acoustic image plane, an acoustic sensor will sense varying vibrational strength levels of the acoustic beams with a lowest vibrational strength level being associated with the acoustic beam(s) farthest from the acoustic sensor at any given moment and a highest vibrational strength level being associated with the acoustic beam(s) closest to the acoustic sensor at any given moment. Consequently, a waveform profile analysis composite acoustic sensing waveform consisting of an array of the acoustic beam sensing waveforms facilitates an estimation of tracking information of each acoustic sensor relative to the acoustic image plane.

The tracking information includes an in-plane location and out-of-plane location of each acoustic sensor and an angular orientation of a spatial alignment of the acoustic sensors.

For purposes of the present invention, the term "out-of-plane location" is broadly defined as any orthogonal location of an acoustic sensor outside of the acoustic image plane.

For purposes of the present invention, the term "in-plane location" is broadly defined herein as a physical location of the acoustic sensor within the acoustic image plane or a projected location of the acoustic sensor within the acoustic image plane derived from a orthogonal projection of the out-of-plane location of the acoustic sensor into the acoustic image plane.

For purposes of the present invention, the term "angular orientation" is broadly defined herein as an angle between the acoustic image plane and a central/rotational axis associated with the spatial alignment of the acoustic sensors. In practice, the spatial alignment of the acoustic sensors may have any form (e.g., straight, curved, helical, etc.).

The present invention recognizes any particular spatial alignment of the acoustic sensors relative to the interventional tool dictates similarities and differences in the profiles of the composite acoustic sensing waveforms, and exploits these similarities and differences in tracking a 3D position of the interventional tool relative to the acoustic image plane. More particularly, for each line trigger of the acoustic imaging device, profile shapes of the composite acoustic sensing waveforms will be similar to a significant degree, particularly for an axial spatial alignment of the acoustic sensors relative to the interventional tool, and profile ranges of the composite acoustic sensing waveforms may be similar or different to an identifiable degree dependent upon the in-plane location and the out-of-plane location of each acoustic sensor.

Specifically, for each acoustic sensor, the peak amplitude of the composite acoustic sensing waveform will identify a 'primary' acoustic beam sensing waveform that is closest to the acoustic sensor whereby a profile of the primary acoustic beam sensing waveform facilitates an estimation of the in-plane location of the acoustic sensor. Computed distances between estimated in-plane locations of the acoustic sensors and knowledge of the spatial distance between the acoustic sensors facilitate an estimation of the angular orientation of the spatial alignment of the acoustic sensors to the acoustic image plane.

Out-of-plane locations of the acoustic sensors may be estimated by a comparison of the relative peak amplitudes of the primary acoustic beam sensing waveforms. These estimation may be supplemented by the in-plane locations of the acoustic sensors and/or the angular orientation of the spatial alignment of the acoustic sensors to the acoustic image plane.

All of the aforementioned location/orientation estimations facilitate a 3D position tracking of the interventional tool, which may be displayed alongside a 2D display of the acoustic image using a variety of known visualization options. To facilitate a further understanding 3D position tracking of the interventional tool in accordance with the present invention, FIGS. 1-8 will now be described herein in the context of an interventional needle 50 having two (2) acoustic sensors 20, 21 spatially aligned on a distal tip of the interventional needle 50 and in the context of use of the interventional needle 50 to perform an amniocentesis procedure involving a 2D acoustic imaging device 10 having a curvilinear array. From the description of FIGS. 1-8, those having ordinary skill in the art will appreciate how to make and use the present invention utilizing various types of interventional tools, acoustic sensors and acoustic imaging devices for various interventional procedures.

FIG. 1 illustrates a 2D ultrasound probe 10 having a curvilinear transducer array for generating an acoustic image plane 11 within an XY plane of an XYZ coordinate system (e.g., an 2D ultrasound probe having a 1D transducer array). Acoustic sensors 20 and 21 sense acoustic image plane 11 with a degree of sensing being dependent upon a proximity of an in-plane location and an out-of-plane location (i.e., collectively XYZ location) of each acoustic sensor 20 and 21 to acoustic image plane 11.

Specifically, each acoustic sensor 20 and 21 will output an acoustic beam sensing waveform indicative of a proximity of the XYZ location of each acoustic sensor 20 and 21 to each beam of acoustic image plane 11. For acoustic beam(s) furthest from the XYZ location of each acoustic sensor 20 and 21, the corresponding acoustic beam sensing waveform will have a ripple wave profile or a zero wave profile. For example, as shown in FIG. 2A, an acoustic beam sensing waveform 30 has a ripple wave indicative of a negligible sensing by an acoustic sensor, if any, of an associated acoustic beam.

Conversely, for acoustic beam(s) closest to the XYZ location of each acoustic sensor 20 and 21, the corresponding acoustic beam sensing waveform will have a fluttering wave profile. For example, as shown in FIG. 2B, acoustic beam sensing waveform 31 has a fluttering wave indicative of a significant sensing by acoustic sensor 20 of an associated acoustic beam. Also by example, as shown in FIG. 2B, acoustic beam sensing waveform 31 has a fluttering wave indicative of a significant sensing by acoustic sensor 21 of an associated beam.

Figure 3B:
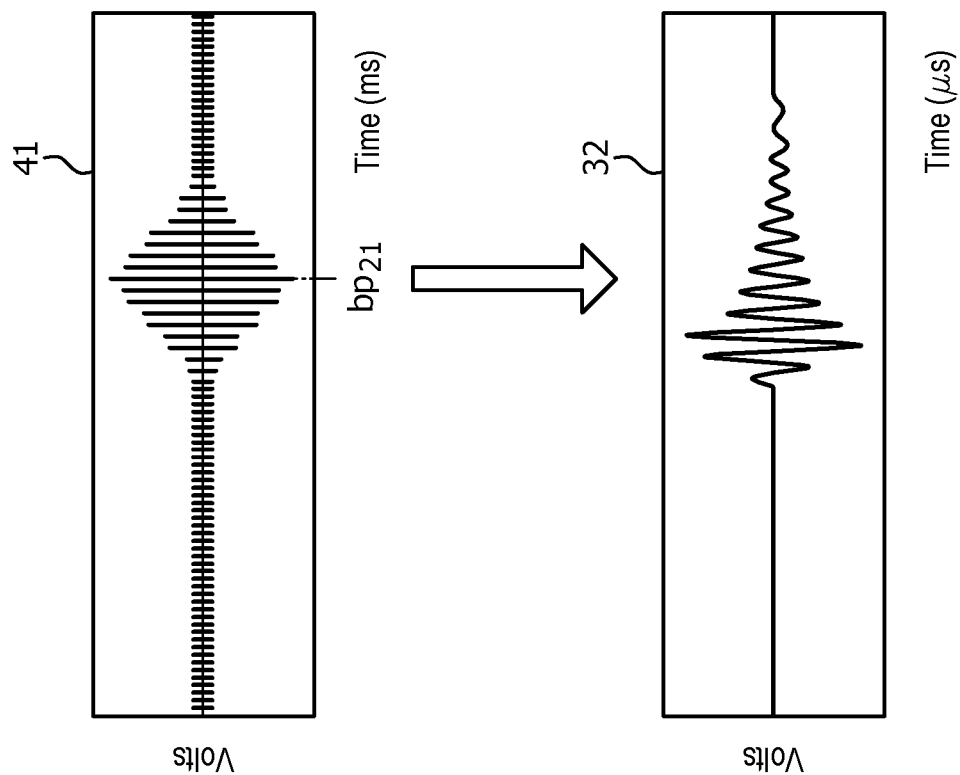
FIGS. 3A and 3B illustrate exemplary primary acoustic beam sensing waveforms of composite acoustic sensing waveforms in accordance with the present invention.
Figure 3A:
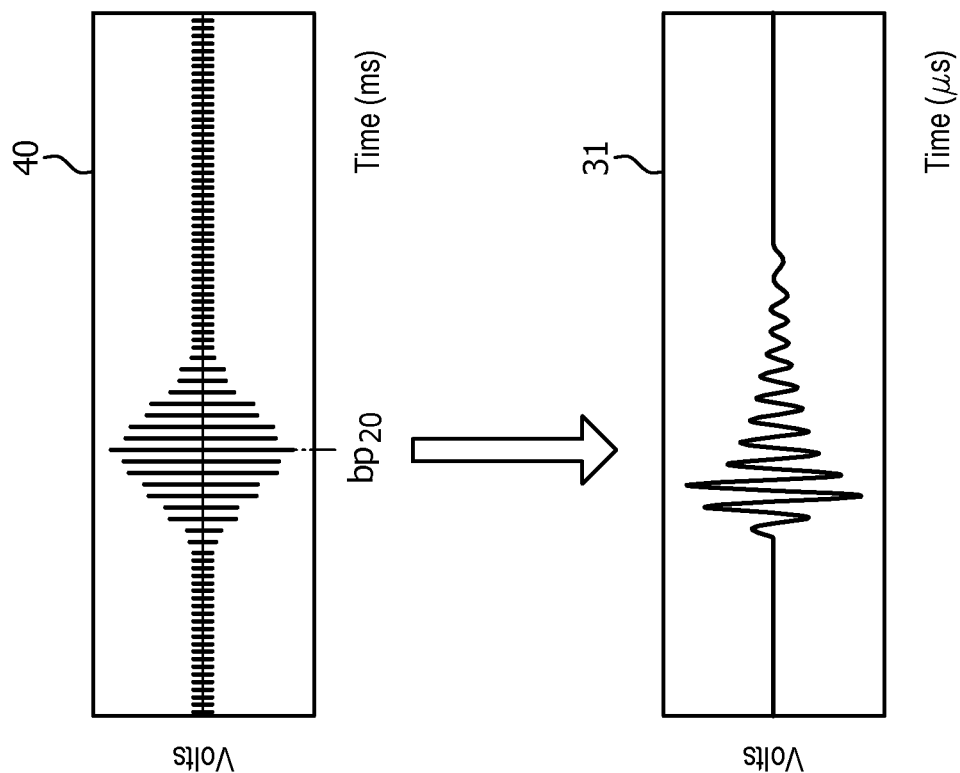

For acoustic image plane 11, each acoustic sensor 20 and 21 will output a composite acoustic sensing waveform including an array of acoustic beam sensing waveforms consisting of ripple/zero wave profiles and fluttering wave profiles in dependence upon a proximity of the XYZ location of each acoustic sensor 20 and 21 to acoustic image plane 11. For example, as shown in FIG. 3A, a composite acoustic sensing waveform 40 includes an array of acoustic beam sensing waveforms consisting of ripple/zero wave profiles and fluttering wave profiles in dependence upon a proximity of the XYZ location of acoustic sensor 20 to acoustic image plane 11. Also by example, as shown in FIG. 3B, a composite acoustic sensing waveform 41 includes an array of acoustic beam sensing waveforms consisting of ripple/zero wave profiles and fluttering wave profiles in dependence upon a proximity of an XYZ location of acoustic sensor 21 to acoustic image plane 11. As previously stated herein, the similarities and differences in composite acoustic sensing waveforms facilitate an estimation of the XYZ locations of acoustic sensors 20 and 21 as well as the spatial alignment of acoustic sensors 20 and 21.

Specifically, determining an XYZ location of each acoustic sensor 20 and 21, a peak amplitude of a corresponding composite acoustic sensing waveform will identify a 'primary' acoustic beam sensing waveform that is closest to the acoustic sensor whereby a profile of the primary acoustic beam sensing waveform facilitates an estimation of an in-plane location and an out-of-plane location of the acoustic sensor.

For example, as shown in FIG. 3A, a peak amplitude of composite acoustic sensing waveform 40 identifies acoustic beam sensing waveform 31 as being the primary acoustic beam sensing waveform. An X coordinate of the in-plane location of acoustic sensor 20 may be estimated based on a beam position $bp_{20}$ of acoustic beam sensing waveform 31 within composite acoustic sensing waveform 40 as shown in FIG. 3A. A Y coordinate of the in-plane location of acoustic sensor 20 may be estimated based on a time $t_{p20}$ of a peak amplitude of acoustic beam sensing waveform 31 as shown in FIG. 2B. A Z coordinate of the out-of-plane location of acoustic sensor 20 may be estimated based on a magnitude $V_{P20}$ of a peak amplitude of acoustic beam sensing waveform 31 as shown in FIG. 2B compared to a maximum peak amplitude of acoustic beam sensing waveform 31 achievable by acoustic sensor 20 being within acoustic image plane 11.

Also by example, as shown in FIG. 3B, a peak amplitude of composite acoustic sensing waveform 41 identifies acoustic beam sensing waveform 32 as being the primary acoustic beam sensing waveform. An X coordinate of the in-plane location of acoustic sensor 21 may be estimated based on a beam position $bp_{21}$ of acoustic beam sensing waveform 32 within composite acoustic sensing waveform 41 as shown in FIG. 3B. A Y coordinate of the in-plane location of acoustic sensor 21 may be estimated based on a time tp21 of a peak amplitude of acoustic beam sensing waveform 32 as shown in FIG. 2C. A Z coordinate of the out-of-plane location of acoustic sensor 21 may be estimated based on a magnitude VP21 of a peak amplitude of acoustic beam sensing waveform 31 as shown in FIG. 2C compared to a maximum peak amplitude of acoustic beam sensing waveform 32 achievable by acoustic sensor 21 being within acoustic image plane 11.

As shown in FIGS. 1A and 1B, acoustic sensor 20 is shown as being closer to probe 10 and acoustic image plane 11 than acoustic sensor 21. Consequently, the XYZ locations of acoustic sensors 20 and 21 as estimated from primary acoustic beam waveforms 31 and 32 will reflect acoustic sensor 20 being closer to probe 10 and acoustic image plane 11 than acoustic sensor 21. Additionally, a comparison to a known spatial alignment 22 of acoustic sensors 20 and 21 to both the in-plane XY locations of acoustic sensors 20 and 21 and a phase offset of acoustic beam sensing waveforms 31 and 32 serves as a basis for estimating an angular orientation θ of a spatial alignment 22 of acoustic sensors 20 and 21 to acoustic image plane 11. The present invention utilizes the estimations of the XYZ locations of acoustic sensors 20 and 21 and an estimation of an angular orientation θ of a known spatial alignment of acoustic sensors 20 and 21 to acoustic image plane 11 as the basis for tracking a position of an interventional tool having acoustic sensors 20 and 21 attached thereto or embedded thereon.

For example, FIGS. 4A-F and 5A-C illustrate a known spatial alignment of acoustic sensors 20 and 21 upon a distal tip of an interventional needle 50. As such, any estimation of the XYZ locations of acoustic sensors 20 and 21 and an estimation of an angular orientation θ of the known spatial alignment of acoustic sensors 20 and 21 to acoustic image plane 11 provides a position of the distal tip of interventional needle 50.

Specifically, FIGS. 4A and 4B illustrate interventional needle 50 being parallel to a X axis of acoustic image plane 11 and interventional needle 50 being perpendicular to a Y axis and a Z axis of acoustic image plane 11. Acoustic sensor 20 outputs a primary acoustic beam waveform 33 shown in FIG. 5A and acoustic sensor 21 outputs a primary acoustic beam waveform 34 as shown in FIG. 5A for estimating the XYZ locations of acoustic sensors 20 and 21 as previously described herein. For this 3D position tracking of interventional needle 50, a zero phase offset PO and a distance of the in-plane locations of acoustic sensors 20 and 21 being equal to the known spatial distance of acoustic sensors 20 and 21 indicate the distal tip of interventional needle 50 is parallel to probe 10 and acoustic image plane 11.

FIGS. 4C and 4D illustrate interventional needle 50 being perpendicular to the X axis and the Z axis of acoustic image plane 11 and interventional needle 50 being parallel to the Y axis of acoustic image plane 11. Acoustic sensor 20 outputs a primary acoustic beam waveform 35 shown in FIG. 5B and acoustic sensor 21 outputs a primary acoustic beam waveform 36 as shown in FIG. 5B for estimating the XYZ locations of acoustic sensors 20 and 21 as previously described herein. For this 3D position tracking of interventional needle 50, a non-zero phase offset PO and distance of the in-plane locations of acoustic sensors 20 and 21 being equal to the known spatial distance of acoustic sensors 20 and 21 indicate the distal tip of interventional needle 50 is perpendicular to probe 10 and parallel to acoustic image plane 11.

FIGS. 4E and 4F illustrate interventional needle 50 being inclined relative to the X axis and the Y axis of acoustic image plane 11. Acoustic sensor 20 outputs a primary acoustic beam waveform 37 shown in FIG. 5C and acoustic sensor 21 outputs a primary acoustic beam waveform 38 as shown in FIG. 5C for estimating the XYZ locations of acoustic sensors 20 and 21 as previously described herein. For this 3D position tracking of interventional needle 50, a zero phase offset and distance of the in-plane locations of acoustic sensors 20 and 21 being less than the known spatial distance of acoustic sensors 20 and 21 indicate the distal tip of interventional needle 50 is parallel to probe 10 and inclined relative to acoustic image plane 11.

From FIGS. FIGS. 4A-F and 5A-C, those having ordinary skill in the art will appreciate the profiles of composite acoustic sensing waveforms outputted by acoustic sensors will change as an interventional tool is navigated relative to an acoustic imaging plane, yet the similarities and differences in the profiles of the composite acoustic sensing waveforms facilitates the 3D relative position tracking of interventional tool.

Furthermore, those having ordinary skill in the art will appreciate equations executed for estimating the XYZ locations of the acoustic sensors and for estimating the angular orientation of the spatial alignment of the acoustic sensors will vary dependent upon a desired tracking resolution.

FIG. 6 further illustrates a tracking workstation 60 for implementing flowchart 80 (FIG. 7) during an amniocentesis procedure of a female patient FP. Tracking workstation 60 is structurally configured with hardware/circuitry (e.g., processor(s), memory, etc.) for executing a network 70 of modules 71-73 as programmed and installed as hardware/software/firmware within tracking workstation 60. In practice, tracking workstation 60 may be an independent workstation or distributed across multiple workstations.

An ultrasound scanner 71 employs technique(s) as known in the art during stage S81 of flowchart 80 (FIG. 7) for controlling a generation of an acoustic image plane 13 by ultrasound probe 12 for imaging a fetus within female patient FP. Ultrasound probe 12 provides imaging data 14 to tracking workstation 60 with imaging data 14 representing a 2D ultrasound image 15 of the fetus of female patient FP.

A tool tracker 72 employs technique(s) of the present invention during stage S82 of flowchart 80 (FIG. 7) to determine a 3D position of a distal tip of interventional needle 50 relative to acoustic image plane 13. In practice, the technique(s) are implemented in accordance with the operating principles of the present invention as previously described herein in connection with FIGS. 1A-5C. In one embodiment, tool tracker 72 implements a flowchart 90 as shown in FIG. 8 that is triggered by a line trigger 74 from ultrasound scanner 71 to tool tracker 72.

Referring to FIGS. 6 and 8, a stage S91 of flowchart 90 encompasses tool tracker 72 processing waveform data 24 of composite acoustic sensing waveforms, such as, for example, composite acoustic sensing waveforms 42 and 43 as shown.

A stage S92 of flowchart 90 encompasses tool tracker 72 estimating an in-plane XY position of each acoustic sensor 20 and 21 as previously described herein.

A stage S93 of flowchart 90 encompasses tool tracker 72 estimating an angular orientation of acoustic sensors 20 and 21 as previously described herein.

A stage S94 of flowchart 90 encompasses tool tracker 72 estimating an out-of-plane location Z of each acoustic sensor 20 and 21 as previously described herein.

In practice, tool tracker 72 may implement flowchart 90 on an instantaneous basis involving a processing of only the most currently composite acoustic sensing waveforms for the estimation stages S92-S94 or on a progressive basis involving a processing of a series of composite acoustic sensing waveforms for the estimation of stages S92-74.

Referring back to FIG. 6, an image tracker 73 employs technique(s) as known in the art during stage S83 of flowchart 80 (FIG. 7) for generating a display 61 of an icon 62 of interventional needle 50 superimposed of a standard view of 2D ultrasound image 15. Alternatively or concurrently, image tracker 71 may generate a display 63 of icon 64 of interventional tool 50 superimposed of a side view of 2D ultrasound image 15.

Referring to FIGS. 1A-8, those having ordinary skill in the art will appreciate numerous benefits of the present invention including, but not limited to, a 3D tracking of interventional tools using acoustic energy generated from an 2D acoustic imaging device.

In practice, various and numerous strategies may be employed to refine the 3D position tracking of the interventional tool via waveform profile analysis of the present invention. For example, it is an indication that the interventional tool is significantly close to the acoustic image plane when peak amplitudes of the composite acoustic sensing waveforms and/or primary acoustic beam waveforms start to 'plateau'. Consequently, the tracking resolution may be increased to refine the accuracy of the tracking of the position of the interventional tool. Also by example, a graph to fit the peak amplitudes of the composite acoustic sensing waveforms and/or primary acoustic beam waveforms may be used to smooth out the waveforms for faster location and angular orientation estimations. By further example, a pre-operative calibration of the acoustic image plane may also be utilized for faster location and angular orientation estimations.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A system, comprising:
a tracking workstation; and
an interventional tool having at least two acoustic sensors,
wherein the at least two acoustic sensors are spatially aligned relative to the interventional tool,
wherein each acoustic sensor of the at least two acoustic sensors is structurally configured to output a composite acoustic sensing waveform including a plurality of acoustic beam sensing waveforms, the composite acoustic sensing waveform being derived from an acoustic sensing of an acoustic image plane,
wherein the tracking workstation is structurally configured to track a position of the interventional tool relative to the acoustic image plane derived from a waveform profile analysis of the composite acoustic sensing waveforms provided by the at least two acoustic sensors,
wherein the waveform profile analysis of the composite acoustic sensing waveforms by the tracking workstation includes an estimation of an in-plane location of the each acoustic sensor as a function of a profile identification of a primary acoustic beam sensing waveform of each of the composite acoustic sensing waveforms, the primary acoustic beam sensing waveform being one of the plurality of acoustic beam sensing waveforms having a largest amplitude, and
wherein an amplitude of each primary acoustic beam sensing waveform is indicative of the in-plane location of a corresponding acoustic sensor,
wherein the waveform profile analysis of the composite acoustic sensing waveforms by the tracking workstation further includes an estimation of an out-of-plane location of the each acoustic sensor as a function of the amplitude of the each primary acoustic beam sensing waveform, and
wherein a comparison of the amplitude of the each primary acoustic beam waveform relative to a profile maximum amplitude is indicative of the out-of-plane location of the each acoustic sensor.

2. The system of claim 1, further comprising:
a probe structurally configured to generate the acoustic image plane.

3. The system of claim 2, wherein the probe is an ultrasound probe.

4. The system of claim 1, wherein the interventional tool is a needle or a catheter.

5. The system of claim 1, wherein the at least two acoustic sensors are at least one of embedded in the interventional tool or attached to the interventional tool.

6. The system of claim 1, wherein a phase of each primary acoustic beam sensing waveform is indicative of the in-plane location of the corresponding acoustic sensor.

7. The system of claim 1, wherein the waveform profile analysis of the composite acoustic sensing waveforms by the tracking workstation further includes:

an estimation of an angular orientation of the interventional tool relative to the acoustic image plane as a function of the estimation of the in-plane location of the each acoustic sensor.

8. The system of claim 7, wherein a phase offset of the primary acoustic beam waveforms is indicative of the angular orientation of the interventional tool relative to the acoustic image plane.

9. The system of claim 7, wherein at least one spatial distance between the at least two acoustic sensors is indicative of the angular orientation of the interventional tool relative to the acoustic image plane.

10. A system, comprising:
a processor;
an interventional tool; and
a plurality of acoustic sensors spatially aligned relative to the interventional tool,
wherein each acoustic sensor of the plurality of acoustic sensors is structurally configured to output a composite acoustic sensing waveform including a plurality of acoustic beam sensing waveforms, the composite acoustic sensing waveform being derived from an acoustic sensing of an acoustic image plane,
wherein the processor is configured to track a position of the interventional tool relative to the acoustic image plane derived from a waveform profile analysis of the composite acoustic sensing waveforms provided by the plurality acoustic sensors,
wherein the waveform profile analysis of the composite acoustic sensing waveforms by the tracking workstation processor includes an estimation of an in-plane location of the each acoustic sensor as a function of a profile identification of a primary acoustic beam sensing waveform of each of the composite acoustic sensing waveforms, the primary acoustic beam sensing waveform being one of the plurality of acoustic beam sensing waveforms having a largest amplitude, and
wherein an amplitude of each primary acoustic beam sensing waveform is indicative of the in-plane location of a corresponding acoustic sensor,
wherein the waveform profile analysis of the composite acoustic sensing waveforms by the processor further includes an estimation of an out-of-plane location of the each acoustic sensor as a function of the amplitude of the each primary acoustic beam sensing waveform, and
wherein a comparison of the amplitude of the each primary acoustic beam waveform relative to a profile maximum amplitude is indicative of the out-of-plane location of the each acoustic sensor.

11. A method for tracking an interventional tool based on a spatial alignment of at least two acoustic sensors relative to the interventional tool, the method comprising acts of:
operating an acoustic imaging device to generate an acoustic image plane;
operating each acoustic sensor of the at least two acoustic sensors to output a composite acoustic sensing waveform including a plurality of acoustic beam sensing waveforms, the composite acoustic sensing waveform being derived from an acoustic sensing of an acoustic image plane; and
operating a tracking workstation to track a position of the interventional tool relative to the acoustic image plane derived from a waveform profile analysis of the composite acoustic sensing waveforms provided by the at least two acoustic sensors, wherein the waveform profile analysis of the composite acoustic sensing waveforms by the tracking workstation includes an estimation of an in-plane location of the each acoustic sensor as a function of a profile identification of a primary acoustic beam sensing waveform of each of the composite acoustic sensing waveforms, the primary acoustic beam sensing waveform being one of the plurality of acoustic beam sensing waveforms having a largest amplitude, and wherein an amplitude of each primary acoustic beam sensing waveform is indicative of the in-plane location of a corresponding acoustic sensor, wherein the waveform profile analysis of the composite acoustic sensing waveforms by the tracking workstation further includes an estimation of an out-of-plane location of the each acoustic sensor as a function of the amplitude of the each primary acoustic beam sensing waveform, and wherein a comparison of the amplitude of the each primary acoustic beam waveform relative to a profile maximum amplitude is indicative of the out-of-plane location of the each acoustic sensor.

12. The method of claim 11, wherein the waveform profile analysis of the composite acoustic sensing waveforms by the tracking workstation further includes:

an estimation of an angular orientation of the interventional tool relative to the acoustic image plane as a function of the estimation of the in-plane location of the each acoustic sensor relative to the acoustic image plane.

13. The method of claim 11, further comprising an act of:

operating the tracking workstation to display the tracked position of the interventional tool relative to an acoustic image derived from the acoustic image plane.

\* \* \* \* \*